United States Patent [19]
Tartaglia et al.

[11] Patent Number: 6,102,926
[45] Date of Patent: *Aug. 15, 2000

[54] APPARATUS FOR PERCUTANEOUSLY PERFORMING MYOCARDIAL REVASCULARIZATION HAVING MEANS FOR SENSING TISSUE PARAMETERS AND METHODS OF USE

[75] Inventors: Joseph M. Tartaglia, Morgan Hill; Vahid Saadat, Redwood Shores; Eric W. Leopold, Redwood City; Peter K. Park, Santa Clara, all of Calif.; Susan Philip, Gladstone, Oreg.

[73] Assignee: Angiotrax, Inc., Sunnyvale, Calif.

[*] Notice: This patent is subject to a terminal disclaimer.

[21] Appl. No.: 09/274,790

[22] Filed: Mar. 23, 1999

Related U.S. Application Data

[63] Continuation-in-part of application No. 08/863,877, May 27, 1997, Pat. No. 5,910,150.
[60] Provisional application No. 60/032,196, Dec. 2, 1996.

[51] Int. Cl.[7] ................................................... A61B 17/32
[52] U.S. Cl. ........................... 606/170; 606/159; 600/564
[58] Field of Search ............................... 606/1, 159, 169, 606/170, 171; 600/564, 565

[56] References Cited

U.S. PATENT DOCUMENTS

| | | |
|---|---|---|
| Re. 33,258 | 7/1990 | Onik et al. . |
| 3,557,794 | 1/1971 | VanPatten . |
| 4,362,161 | 12/1982 | Reimels et al. . |
| 4,576,162 | 3/1986 | McCorkle . |
| 4,582,056 | 4/1986 | McCorkle . |
| 4,640,296 | 2/1987 | Schnepp-Pesch et al. . |
| 4,646,738 | 3/1987 | Trott . |
| 4,729,763 | 3/1988 | Henrie . |
| 4,813,930 | 3/1989 | Elliott . |
| 4,895,166 | 1/1990 | Farr et al. . |

(List continued on next page.)

FOREIGN PATENT DOCUMENTS

| | | |
|---|---|---|
| 0868 923A2 | 7/1998 | European Pat. Off. . |
| 0876 796A2 | 11/1998 | European Pat. Off. . |
| 0895 752A1 | 10/1999 | European Pat. Off. . |
| WO 96/26675 | 9/1996 | WIPO . |
| WO98/05307 | 2/1998 | WIPO . |
| WO98/38916 | 9/1998 | WIPO . |
| WO98/39045 | 9/1998 | WIPO . |

OTHER PUBLICATIONS

Cooley, Denton A., M.D. et al., "Transmyocardial Laser Revascularization: Anatomic Evidence of Long–Term Channel Patency," *Texas heart Institute Journal*, vol. 21, No. 3 (1994), pp. 220–224.

Cooley, Denton A., M.D. et al., "Transmyocardial Laser Revascularization: Clinical Experience with Twelve–Month Follow–Up," *The Journal of Thoracic and Cardiovascular Surgery*, (Apr. 1996), pp. 791–799.

(List continued on next page.)

*Primary Examiner*—Michael Buiz
*Assistant Examiner*—William W Lewis
*Attorney, Agent, or Firm*—Fish & Neave; Nicola A. Pisano

[57] ABSTRACT

Apparatus and methods for percutaneously performing myocardial revascularization are provided using a catheter having an end region that is directable to contact a patient's endocardium at a plurality of positions. A cutting head is disposed within a lumen of the catheter and coupled to a drive tube that rotates and reciprocates the drive shaft. One or more stabilizing elements are disposed on the distal end to retain the catheter in position when the cutting head is actuated. The cutting head and drive tube include a lumen through which severed tissue is aspirated. Mechanisms and methods are provided for providing the operator with information to assess the desirability of treating a proposed site. Mechanisms also are provided for controlling the maximum extension of the cutting head beyond a distal endface of the catheter, independent of the degree of tortuosity imposed on the catheter.

45 Claims, 9 Drawing Sheets

U.S. PATENT DOCUMENTS

| | | |
|---|---|---|
| 4,923,462 | 5/1990 | Stevens . |
| 4,976,710 | 12/1990 | Mackin . |
| 5,093,877 | 3/1992 | Aita et al. . |
| 5,104,393 | 4/1992 | Isner et al. . |
| 5,106,386 | 4/1992 | Isner et al. . |
| 5,152,744 | 10/1992 | Krause et al. . |
| 5,242,460 | 9/1993 | Klein et al. . |
| 5,281,218 | 1/1994 | Imran . |
| 5,285,795 | 2/1994 | Ryan et al. . |
| 5,323,781 | 6/1994 | Ideker et al. . |
| 5,324,284 | 6/1994 | Imran . |
| 5,330,466 | 7/1994 | Imran . |
| 5,336,237 | 8/1994 | Chin et al. . |
| 5,342,300 | 8/1994 | Stefanadis et al. . |
| 5,354,310 | 10/1994 | Garnic et al. . |
| 5,358,472 | 10/1994 | Vance et al. . |
| 5,358,485 | 10/1994 | Vance et al. . |
| 5,379,772 | 1/1995 | Imran . |
| 5,380,316 | 1/1995 | Aita et al. . |
| 5,383,884 | 1/1995 | Summers . |
| 5,389,073 | 2/1995 | Imran . |
| 5,389,096 | 2/1995 | Aita et al. . |
| 5,403,334 | 4/1995 | Evans et al. . |
| 5,409,000 | 4/1995 | Imran . |
| 5,415,166 | 5/1995 | Imran . |
| 5,439,474 | 8/1995 | Li . |
| 5,443,443 | 8/1995 | Shiber . |
| 5,465,717 | 11/1995 | Imran et al. . |
| 5,488,958 | 2/1996 | Topel et al. . |
| 5,497,784 | 3/1996 | Imran . |
| 5,505,725 | 4/1996 | Samson . |
| 5,507,802 | 4/1996 | Imran . |
| 5,520,634 | 5/1996 | Fox et al. . |
| 5,527,279 | 6/1996 | Imran . |
| 5,554,152 | 9/1996 | Aita et al. . |
| 5,562,694 | 10/1996 | Sauer et al. . |
| 5,569,178 | 10/1996 | Henley . |
| 5,569,284 | 10/1996 | Young et al. . |
| 5,575,772 | 11/1996 | Lennox . |
| 5,575,787 | 11/1996 | Abela et al. . |
| 5,578,067 | 11/1996 | Ekwall et al. . |
| 5,591,159 | 1/1997 | Taheri . |
| 5,601,573 | 2/1997 | Fogelberg et al. . |
| 5,601,586 | 2/1997 | Fucci et al. . |
| 5,601,588 | 2/1997 | Tonomura et al. . |
| 5,607,421 | 3/1997 | Jeevanandam et al. . |
| 5,609,591 | 3/1997 | Daikuzono . |
| 5,609,621 | 3/1997 | Bonner . |
| 5,611,803 | 3/1997 | Heaven et al. . |
| 5,643,253 | 7/1997 | Baxter et al. . |
| 5,651,781 | 7/1997 | Grace . |
| 5,662,124 | 9/1997 | Wilk . |
| 5,662,671 | 9/1997 | Barbut et al. . |
| 5,702,412 | 12/1997 | Popov et al. ............................. 606/153 |
| 5,724,975 | 3/1998 | Negus et al. . |
| 5,725,521 | 3/1998 | Mueller . |
| 5,782,823 | 7/1998 | Mueller . |
| 5,807,384 | 9/1998 | Mueller . |
| 5,830,210 | 11/1998 | Rudko et al. . |
| 5,830,222 | 11/1998 | Makower . |
| 5,840,059 | 11/1998 | March et al. . |
| 5,871,495 | 2/1999 | Mueller . |
| 5,893,848 | 4/1999 | Negus et al. . |
| 5,968,059 | 10/1999 | Ellis et al. . |
| 5,980,545 | 11/1999 | Pacala et al. . |
| 5,989,278 | 11/1999 | Mueller . |

OTHER PUBLICATIONS

Frazier, O.H., M.D., "Myocardial Revascularization With Laser: Preliminary Findings," *Supplement II Circulation*, vol. 92, No. 9, (Nov. 1995), pp. II–58–II–65.

Hardy, Roger Ian, "A Histologic Study of Laser–Induced Transmyocardial Channels," *Lasers in Surgery and Medicine*, (1987), pp. 6:563–573.

Hershey, John E. et al., "Transmyocardial Puncture Revascularization: A Possible Emergency Adjunct to Arterial Implant Surgery," *Geriatrics*, (Mar. 1969), pp. 101–108.

Horvath, Keith A., M.D., et al., "Recovery and Viability of an Acute Myocardial Infarct After Transmyocardial Laser Revascularization," *Journal of American College of Cardiology*, vol. 25, No. 1 (Jan. 1995), pp. 258–263.

Horvath, Keith A., M.D., et al., "Transmyocardial Laser Revascularization: Operative Techniques and Clinical Results at Two Years," *The Journal of Thoracic and Cardiovascular Surgery*, (May 1996) pp. 1047–1053.

*PMR Product, Axcis$^{198}$ PMR$^{198}$ System, http://www.cardiogenesis.com/ percutaneous/product.html, Jan. 27, 1999.

*The PMR$^{198}$ Procedure, http://www.cardiogenesis.com/percutaneous/ procedure.html, Jan. 27, 1999.

Kohmoto, Takushi, M.D., "Does Blood Flow Through Holmium: YAG Transmyocardial Lase Channels?," *Ann. Thorac. Surg.*, (1996) pp. 61: 861–868.

Lee, Gilbert, M.D., "Effects of Laser Irradiation Delivered by Flexible Fiberoptic System on the Left Ventricular Internal Myocardium," *American Heart Journal*, (Sep. 1983), pp. 587–590.

NASA's Jet Propulsion Laboratory, Swivel–Head Sampling Drill Bit, *NASA Tech Briefs*, p. 67, Nov. 1998.

Sen, P.K. et al., "Further Studies in Multiple Transmyocardial Acupuncture as a Method of Myocardial Revascularization," *Surgery*, vol. 62, No. 5, (Nov. 1968), pp. 861–870.

Thaning, Otto, "Transmyocardial Laser Revascularisation in South Africa," *SAMJ*, vol. 85, No. 9 (Aug. 1995) pp. 787–788.

Von Oppell, Ulrich O., "Transmyocardial Laser Revascularisation," *SAMJ*, vol. 85, No. 9, (Sep. 1995), p. 930.

White, Manuel et al., "Multiple Transmyocardial Puncture Revascularization in Refractory Ventricular Fibrillation due to Myocardial Ischemia," *The Annals of Thoracic Surgery*, vol. 6, No. 6, (Dec. 1968), pp. 557–563.

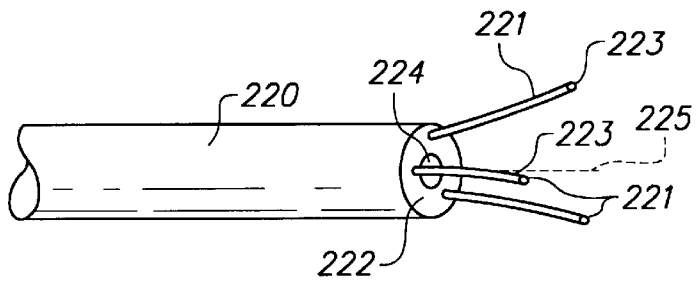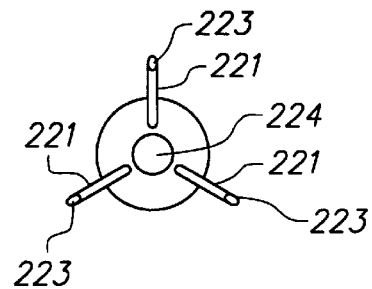
FIG. 15A                FIG. 15B
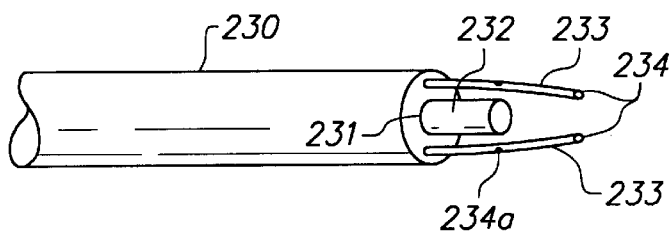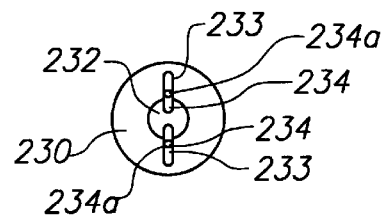
FIG. 16A                FIG. 16B
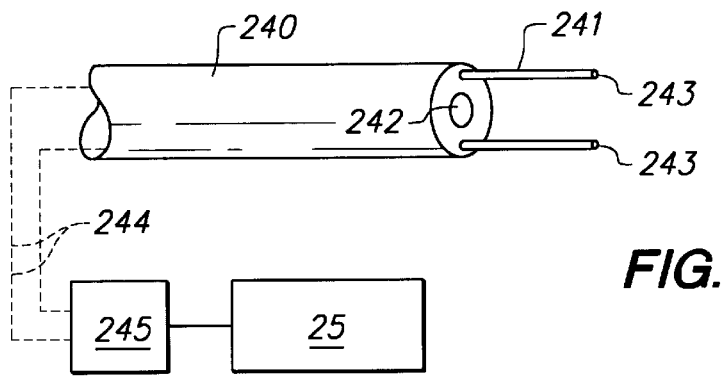
FIG. 17
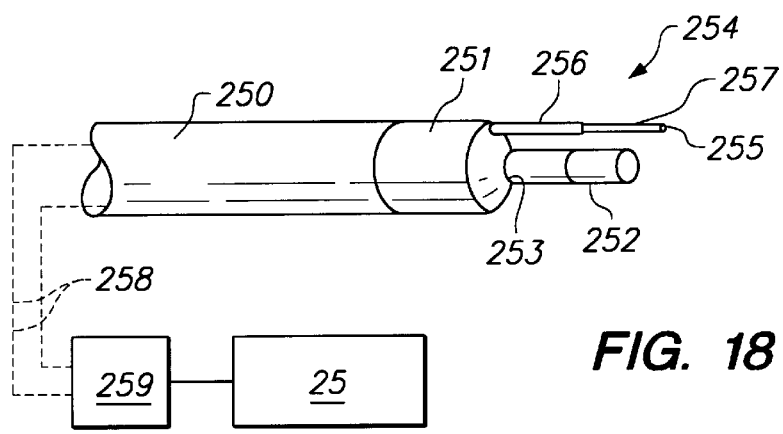
FIG. 18

APPARATUS FOR PERCUTANEOUSLY PERFORMING MYOCARDIAL REVASCULARIZATION HAVING MEANS FOR SENSING TISSUE PARAMETERS AND METHODS OF USE

REFERENCE TO RELATED APPLICATIONS

The present application is a continuation-in-part of U.S. patent application Ser. No. 08/863,877, filed May 27, 1997, now U.S. Pat. No. 5,910,150, which claims the benefit of the filing date of U.S. provisional patent application Ser. No. 60/032,196, filed Dec. 2, 1996.

FIELD OF THE INVENTION

The present invention relates to apparatus and methods for percutaneously performing myocardial revascularization. More particularly, the present invention provides a device that enables a clinician to perform myocardial revascularization by treating only those regions of cardiac tissue likely to experience beneficial effect.

BACKGROUND OF THE INVENTION

A leading cause of death in the United States today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

One technique that has been developed to treat patients suffering from diffuse atherosclerosis, is referred to as transmyocardial revascularization (TMR). In this method, a series of channels are formed in the left ventricular wall of the heart. Typically, between 15 and 30 channels about 1 mm in diameter and preferably several millimeters deep are formed with a laser in the wall of the left ventricle to perfuse the heart muscle with blood coming directly from the inside of the left ventricle, rather than traveling through the coronary arteries. Apparatus and methods have been proposed to create those channels both percutaneously and intraoperatively (i.e., with the chest opened).

U.S. Pat. No. 5,389,096 to Aita et al. describes a catheter-based laser apparatus for use in percutaneously forming channels extending from the endocardium into the myocardium. The catheter includes a plurality of control lines for directing the tip of the catheter. The patent states that because the myocardium is more easily traversed than the epicardium, the clinician may judge the depth of the channel by sensing the pressure applied to the proximal end of the catheter. The patent does not address the problem of cardiac tamponade that might result if the clinician inadvertently perforates the heart wall, nor how ablated tissue is prevented from embolizing blood vessels. Moreover, Aita et al. rely on fluoroscopic methods to determine the location of the distal end of the catheter.

U.S. Pat. No. 5,591,159 to Taheri describes a mechanical apparatus for performing TMR involving a catheter having an end effector formed from a plurality of spring-loaded needles. The catheter first is positioned percutaneously within the left ventricle. A plunger is then released so that the needles are thrust into the endocardium. The needles form small channels that extend into the myocardium as they are withdrawn. The patent suggests that the needles may be withdrawn and advanced repetitively at different locations under fluoroscopic guidance. The patent does not appear to address how tissue is ejected from the needles between the tissue-cutting steps.

The disadvantages of the above-described previously known methods and apparatus for performing TMR are numerous and will impede the acceptance of this new treatment method. For example, percutaneous laser-based systems, such as described in the Aita et al. patent, do not provide the ability to reliably determine the depth of the channels formed by the laser and may result in perforations, nor does that system address potential embolization of the ablated tissue. Likewise, previously known mechanical systems do not address issues such as how to remove tissue cores from the needles. Neither do such previously known systems provide the capability to assess whether channel formation or drug injection at a proposed site will provide any therapeutic benefit.

U.S. Pat. No. 5,910,150 (allowed U.S. patent application Ser. No. 08/863,877, filed May 27, 1997), which is incorporated herein by reference, describes a percutaneous system for performing TMR that uses a rotating tubular cutting head disposed for reciprocation beyond the end face of a catheter. Vacuum drawn through the cutting head aspirates the severed tissue, thus reducing the risk of embolization.

A drawback common to all of the previously known percutaneous myocardial revascularization devices is the inability to determine whether treating a proposed site, such as by forming a channel in the myocardium or by injecting drugs or angiogenic agents, would have a therapeutic effect. For example, little therapeutic benefit would be expected from forming channels or injecting drugs or angiogenic agents in heavily infarcted tissue. It would therefore be desirable to provide apparatus and methods that enable a clinician to determine whether treatment at a proposed site would be beneficial.

It has been observed that in the device described in the above-incorporated patent, the distance that the cutting head extends into the tissue depends upon the degree of tortuosity imposed on the catheter when percutaneously inserting the distal end of the catheter into the left ventricle. This is so because differences in the radii of curvature of the catheter and the drive tube coupled to the cutting head can result in significant accumulated displacement of the cutting head relative to the distal endface of the catheter. This displacement effect is heightened where the tip of the catheter is articulated using a pull wire that exerts a compressive force on the catheter.

Accordingly, it also would be desirable to provide apparatus and methods for percutaneously performing myocardial revascularization that enable a reciprocated cutting head to be advanced a controlled depth, independent of the degree of tortuosity imposed on the catheter.

It further would be desirable to control the location within the ventricle of a distal end of a device for percutaneously performing myocardial revascularization, both with respect to features of the ventricular walls and in relation to other channels formed by the device.

It still further would be desirable to provide apparatus and methods for percutaneously performing myocardial revascularization that enable therapeutic agents, such as angiogenic growth factors, genes, or drugs to be injected into the myocardium within or adjacent to channels formed by the cutting head.

It also would be desirable to provide the capability to stabilize a distal end of a device for percutaneously performing myocardial revascularization, for example, to counteract reaction forces created by the actuation of the cutting head, and to reduce transverse movement of the distal end of the device.

It further would be desirable to provide apparatus and methods for percutaneously performing myocardial revascularization that use cutting heads designed to morcellate severed tissue to enhance aspiration of the severed tissue from the treatment site.

SUMMARY OF THE INVENTION

In view of the foregoing, it is an object of this invention to provide apparatus and methods for percutaneously performing myocardial revascularization that enable a clinician to determine during a percutaneous myocardial revascularization procedure whether treatment at a proposed site would be beneficial.

It is another object of the present invention to enable a reciprocated cutting head to be advanced to a controlled depth, independent of the degree of tortuosity imposed on the catheter.

It is also an object of the present invention to provide apparatus and methods that enable control of the location within the ventricle of a distal end of a device for percutaneously performing myocardial revascularization, both with respect to features of the ventricular walls and in relation to other channels formed by the device.

It is a further object of the present invention to provide apparatus and methods for percutaneously performing myocardial revascularization that enable therapeutic agents, such as angiogenic growth factors, genes, plasmids or drugs to be injected into the myocardium or channels formed by the cutting head.

It is another object of this invention to provide apparatus and methods to stabilize a distal end of a device for percutaneously performing myocardial revascularization, for example, to counteract reaction forces created by the actuation of the cutting head and to reduce transverse movement of the distal end of the device.

It is a still further object of the present invention to provide apparatus and methods for percutaneously performing myocardial revascularization that use cutting heads designed to morcellate severed tissue to enhance aspiration of the severed tissue from the treatment site.

These and other objects of the present invention are accomplished by providing apparatus that senses a physiologic parameter, e.g., electrical activity or impedance, of tissue at a proposed treatment site, and providing information to the operator indicative of a state of the tissue. The operator then uses that information in deciding whether to form a channel or inject drugs into that region tissue, or to re-position the device elsewhere.

Apparatus constructed in accordance with the present invention comprises a catheter having an end region that is directable to contact a patient's endocardium at a plurality of positions. Preferably, the catheter comprises inner and outer catheters each having preformed distal bends, so that the distal end of the inner catheter is directable to a plurality of positions. A cutting head is disposed within a lumen of the inner catheter and coupled to a drive tube that rotates and reciprocates the drive shaft. The drive tube is coupled to a motor that imparts rotational motion to the drive tube. One or more stabilizing elements are disposed on the distal end to retain the inner catheter in position while the cutting head is reciprocated beyond a distal endface of the inner catheter. The cutting head and drive tube include a lumen through which severed tissue is aspirated.

In accordance with another aspect of the present invention, means are provided for limiting the maximum extension of the cutting head beyond the distal endface of the catheter, independent of the degree of bending imposed on the inner catheter and drive tube. In one embodiment, in which the drive tube and cutting head are reciprocated by a linear actuator mechanism, the drive tube includes a bearing surface that abuts against a mating surface affixed within a distal region of the inner catheter, and circuitry that senses a parameter (e.g., stall torque or linear force) of a motor driving the drive tube. When the bearing surface contacts the mating surface, the increase in the motor parameter is sensed, forward motion ceases, and the direction of travel of the linear actuator mechanism is reversed.

In another embodiment, the drive tube and cutting head are reciprocated manually, the drive tube includes a bearing surface that abuts against a mating surface affixed within a distal region of the inner catheter, and the mechanism used to advance the drive tube transmits to the user sufficient tactile sensation for the user to detect that the maximum depth has been achieved. The handle of the device may optionally include a mechanism for adjusting the position of the distal endface of the inner catheter relative to the cutting head, to account for differences in the curvatures of the inner catheter and drive tube.

In still other alternative embodiments, the opposing bearing surfaces may be omitted, and attainment of the maximum cutting depth may be sensed by a mechanical switch, a resistance-based circuit or an optical circuit. In these embodiments, the maximum extension of the cutting head may be set independently of the adjustment required to reduce or eliminate any displacement effect caused by bending of the catheter.

Methods of using the apparatus of the present invention to selectively form channels and/or inject therapeutic agents in the myocardium are also provided.

BRIEF DESCRIPTION OF THE DRAWINGS

Further features of the invention, its nature and various advantages will be more apparent from the accompanying drawings and the following detailed description of the preferred embodiments, in which:

FIGS. 15A–15B are, respectively, side and end views of the distal region of a further alternative embodiment of the inner catheter of the present invention;

FIGS. 16A–16B are, respectively, side and end views of the distal region of another alternative embodiment of the inner catheter of the present invention;

FIG. 17 is a partial schematic view of an embodiment of the present invention that permits measurement of a physiologic parameter of tissue prior to channel formation and/or injection of therapeutic agent; and FIG. 18 is a partial schematic view of an alternative embodiment of the present invention that permits measurement of a physiologic parameter of tissue prior to channel formation and/or injection of therapeutic agent.

DETAILED DESCRIPTION OF THE INVENTION

The present invention provides apparatus and methods for percutaneously performing myocardial revascularization by mechanically cutting a series of channels in the myocardium using a rotating cutting head and aspirating the severed tissue. The cutting head is disposed within a lumen of a catheter, and is extended beyond a distal endface of the catheter to bore a channel. In accordance with the principles of the present invention, a physiologic parameter is measured at a proposed treatment site, and that information is provided to the operator to assess whether to treat that site or re-position the device. The apparatus and methods of the present invention further provide for limiting the maximum extension of the cutting head, independent of the tortuosity of the path traversed by the catheter. The maximum extension of the cutting head also may be independently adjusted.

Figure 1:
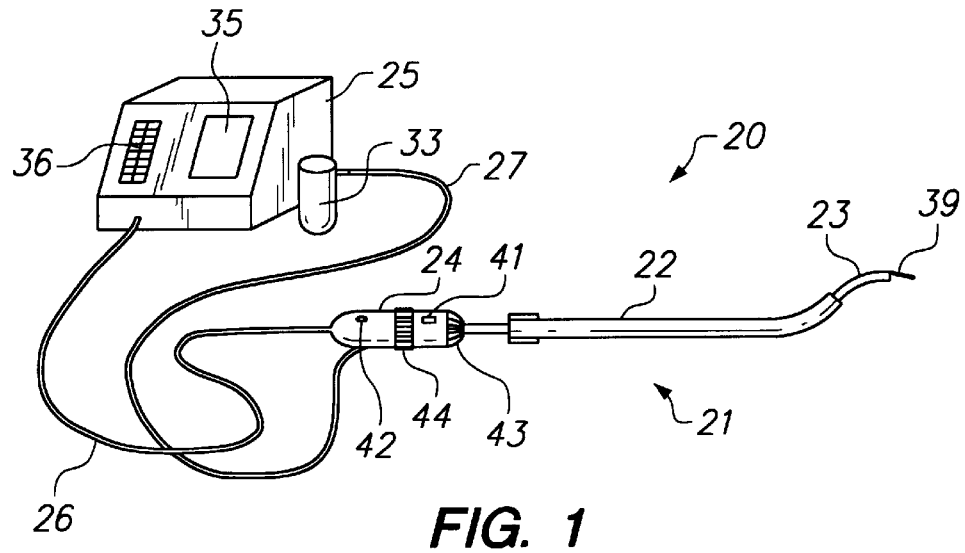
FIG. 1 is a perspective view of an illustrative embodiment of apparatus constructed in accordance with the present invention.
Figure 2:
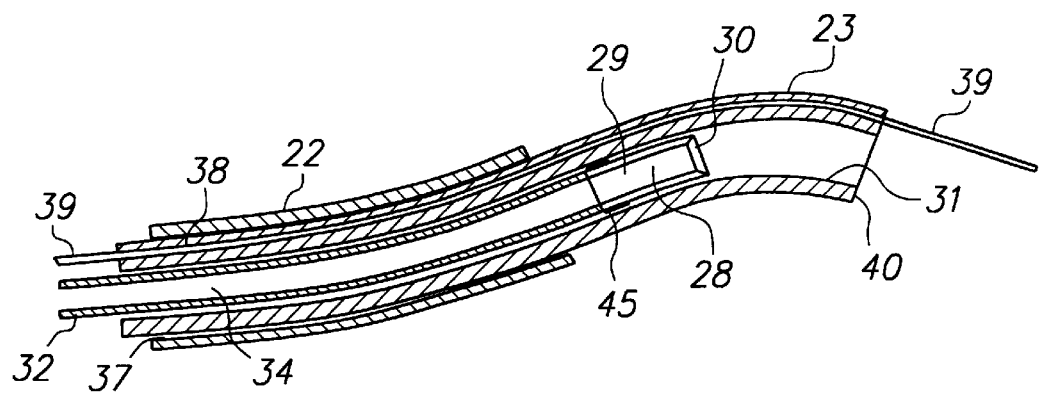
FIG. 2 is a partial sectional view of the distal region of the apparatus of FIG. 1.

Referring to FIGS. 1 and 2, illustrative apparatus 20 constructed in accordance with the present invention is described. Apparatus 20 includes device 21 comprising handle 24 having inner catheter 23 disposed within outer guide catheter 22, and coupled to controller 25 via cable 26 and vacuum hose 27. Cutting head 28 having lumen 29 and sharpened distal end 30 is disposed within lumen 31 of inner catheter 23. Cutting head 28 is coupled to drive tube 32, which in turn is coupled via cable 26 to a drive system contained in controller 25 that imparts rotational and longitudinal motion to drive tube 32 and cutting head 28. Suction is drawn through lumen 29 of cutting head 28 and drive tube 32 to aspirate tissue severed by the cutting head to tissue trap 33 connected to controller 25 via vacuum hose 27.

Controller 25 comprises a vacuum pump or vacuum canister (not shown) that draws suction through lumen 34 of drive tube 32 via hose 27, a drive train (not shown) including a motor and gearing that impart rotational motion to drive tube 32 via cable 26, and a linear actuator mechanism (e.g., electromechanical or pneumatic) that reciprocates drive tube 32 and cutting head 28 within lumen 31 of inner catheter 23. Controller 25 also includes display panel 35, input panel 36 (e.g., a plurality of selector switches) and circuitry (see FIG. 5) for controlling operation of device 21. Further details of controller 25 are described in U.S. Pat. No. 5,910,150 (allowed U.S. patent application Ser. No. 08/863,877, filed May 27, 1997), which is again incorporated herein by reference.

Inner catheter 23 is disposed for movement, either rotational, longitudinal or both, within lumen 37 of outer guide catheter 22. Inner catheter 23 further includes lumen 38 through which needle stabilizer 39 may be reciprocated from a retracted position, within lumen 38, to an extended position, extending beyond distal endface 40 of inner catheter 23 (as shown in FIG. 2). A proximal end of needle stabilizer 39 is coupled to slider button 41 of handle 24. When moved to the extended position, needle stabilizer 39 retains the distal end of inner catheter 23 in position with respect to an endocardial surface, and counteracts reaction forces generated when cutting head 28 is actuated.

Figure 3:
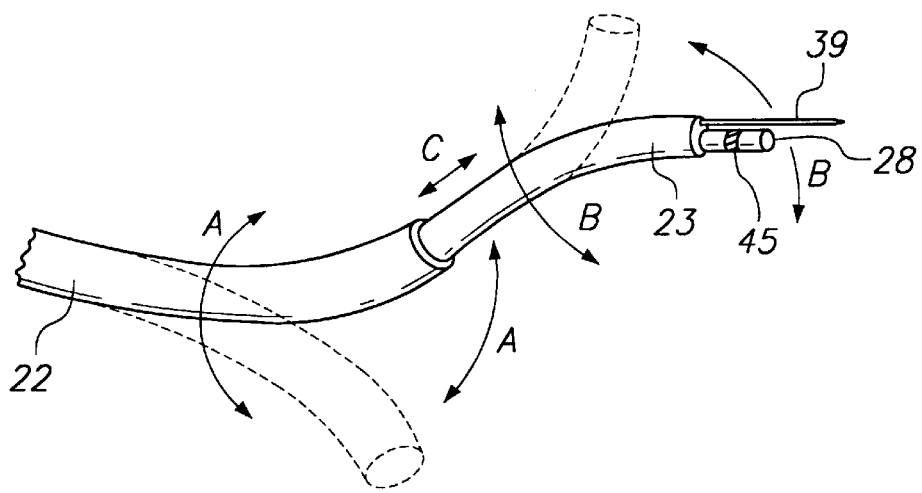
FIG. 3 is a perspective view illustrating how the inner and outer catheters can be rotated to position the distal end of the inner catheter at a plurality of positions.

Cutting head 28 and drive tube 32 are coupled via cable 26 to a drive train that moves cutting head 28 from a retracted position within lumen 31 of inner catheter 23 (as shown) in FIG. 2), to an extended position wherein cutting head 28 and a distal portion of drive tube 32 extend beyond distal endface 40 (see FIG. 3). Button 42 of handle 24 signals controller 25 to extend and rotate cutting head 28 to cut a channel in the myocardium. Myocardial tissue severed by cutting head 28 is aspirated through lumen 34 of drive tube 32 to tissue trap 33 to reduce the risk that the severed tissue will embolize. Cutting head 28 preferably is constructed of a radio-opaque material or includes band 45 of radio-opaque material, such as platinum-iridium, disposed on its proximal end to assist in visualizing the location of the cutting head under a fluoroscope.

Referring to FIG. 3, outer guide catheter 22 and inner catheter 23 preferably include preformed bends. In particular, by rotating outer guide catheter 22 (indicated by arrows A) or inner catheter 23 (as indicated by arrows B) relative to one another, or extending inner catheter 23 longitudinally with respect to outer guide catheter 22 (as indicated by arrows C), distal endface 40 of inner catheter 23 may be disposed at a plurality of tissue contacting locations. Accordingly, outer guide catheter may disposed at a first orientation relative to an endocardial surface, and then inner catheter 23 may be moved relative to outer catheter 22 to form channels at a plurality of positions along the path indicated by arrows B. Outer catheter 22 may then be moved along the path indicated by arrows A, and a new series of holes may then be formed at that position by further rotating inner catheter 23. As will of course be understood, needle stabilizer 39 and cutting head 28 are retracted when moving between one channel forming position and another.

Figure 4A:
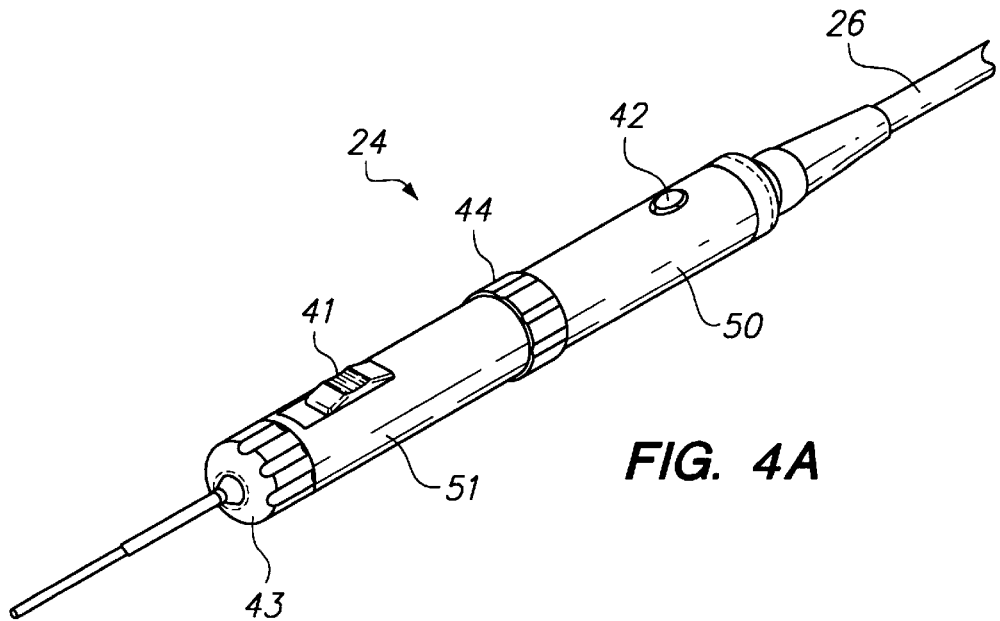
FIGS. 4A and 4B are, respectively, a perspective view and sectional view of an illustrative handle of the apparatus of FIG. 1.
Figure 4B:
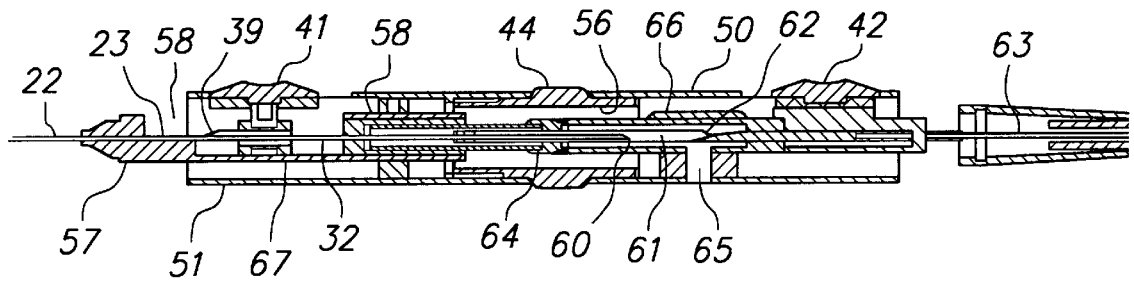

Referring now to FIGS. 4A and 4B, an illustrative arrangement of the components of handle 24 is described. Handle 24 comprises proximal and distal portions 50 and 51, respectively, joined so that distal portion 51 may be rotated independently of proximal portion 50. Proximal portion 50 is coupled to cable 26 and includes button 42 for activating the cutting head to bore a channel. Distal portion 51 is affixed to inner catheter 23 so that rotation of knob 43 of portion 51 is transmitted to the distal end of inner catheter 23.

Slider button 41 is coupled to needle stabilizer 39, so that movement of button 41 in the distal direction deploys needle stabilizer 39, and movement of button 41 in the proximal direction retracts needle stabilizer 39 within lumen 38 of inner catheter 23. Needle stabilizer 39 may comprise a solid wire element, or may include a lumen through which therapeutic agents may be injected, as described hereinbelow. Wheel 44, if provided, is coupled to inner catheter 23 to permit optional adjustment of the cutting depth attained by cutting head 28.

With respect to FIG. 4B, wheel 44 is disposed within tubular member 56 and extends within portions 50 and 51. Inner catheter 23 is coupled to a rigid tubular member (e.g., stainless steel hypotube) that extends through element 57. Element 57 in turn is coupled through tubular member 58 to distal portion 51, so that rotation of distal portion 51 is transmitted to inner catheter 23. Tubular member 56 is coupled by threads to tubular member 58 so that rotation of wheel 44 causes inner catheter to be moved in a distal or proximal direction relative to drive tube 32 (depending upon direction of rotation), thereby lengthening or shortening the stroke of cutting head 28 beyond distal endface 40 of the inner catheter.

Drive tube 32 has proximal end 60 affixed to tubular member 61 having skive 62. Tubular member 61 is coupled to drive wire 63. Tubular member 61 is disposed for rotational and longitudinal motion, imparted by drive wire 63, within tubular member 64. The distal end of tubular member 64 is disposed within tubular member 58, while the proximal end includes a suitable bearing that seals against tubular member 61 without binding. Tissue passing through lumen 34 of drive tube 32 exits through skive 62 into the interior of tubular member 64, and then aspirated through port 65 into vacuum hose 27. Tubular member 64 is affixed to the interior of proximal portion 51 by element 66, which also supports button 42. Needle stabilizer 39 is fastened to slider button 41, which is in turn coupled to spool 67 to provide rigidity to the assembly.

Handle 24 therefore provides the ability to rotate distal portion 51 of the handle to orient the bend in inner catheter 23, while retaining button 42 on top of proximal portion 50 facing upward. Slider button 41 permits needle stabilizer 39 to be selectively deployed, and knob 43 permits the inner catheter to be rotated relative to the outer guide catheter. Wheel 44 permits the inner catheter to be translated distally or proximally with respect to the cutting head, to account for the effects of inserting the distal portion of device 21 along a tortuous path.

Figure 5:
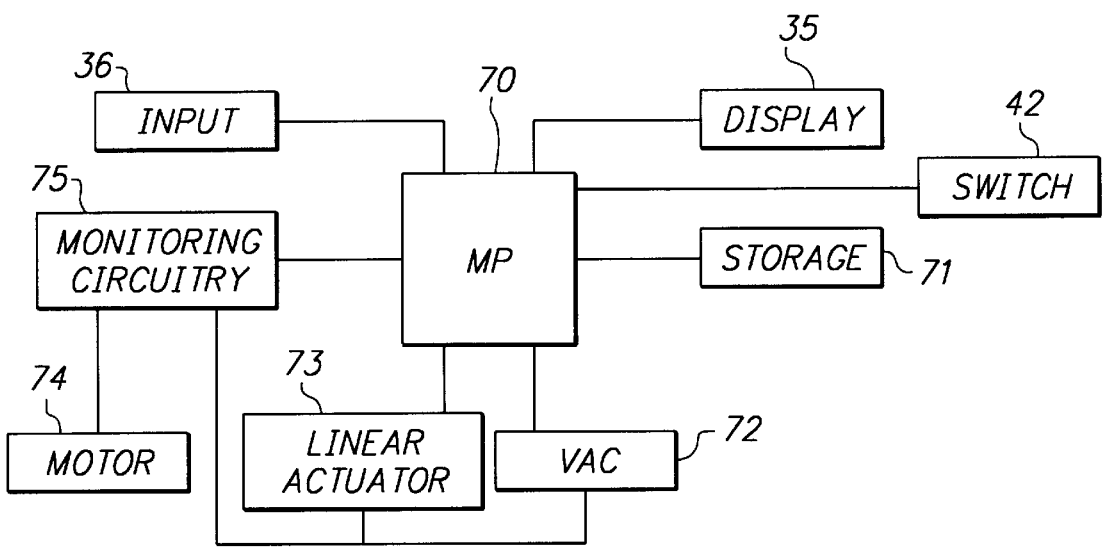
FIG. 5 is a block diagram of the components of a controller constructed in accordance with the present invention.

With respect to FIG. 5, a block diagram of the components of controller 25 are described. Controller 25 preferably comprises microprocessor 70 coupled to display panel 35, input device 36 (e.g., keyboard), activation button 42 of handle 24, data storage 71 (e.g., RAM and ROM or hard disk), vacuum pump 72, linear actuator mechanism 73 (e.g., a worm screw drive or pneumatic cylinder), motor 74 and monitoring circuitry 75. Monitoring circuitry 75 may be coupled to components 72–74, for example, to monitor the level of vacuum drawn by vacuum pump 72, or a motor parameter, such as the displacement of or linear force applied by linear actuator mechanism 73 and/or the speed of or electrical current drawn by motor 74.

For example, monitoring circuitry 75 may be arranged to ensure that the cutting head is not extended unless there is an appropriate level of suction being drawn through drive tube 32 and cutting head 28, or that the cutting head is rotating at a desired RPM before being advanced into tissue.

Additional applications for monitoring circuitry 75 are described in the above-incorporated, commonly assigned U.S. patent. In a preferred embodiment of the present invention, monitoring circuitry 75 is configured to limit and/or adjust the cutting depth attained by the cutting head, as described in detail below. Controller 25 also may comprise circuitry for measuring a physiologic parameter of tissue, e.g., impedance or electrical activity, as described hereinbelow with respect to the embodiments of FIGS. 17 and 18.

Figure 6:
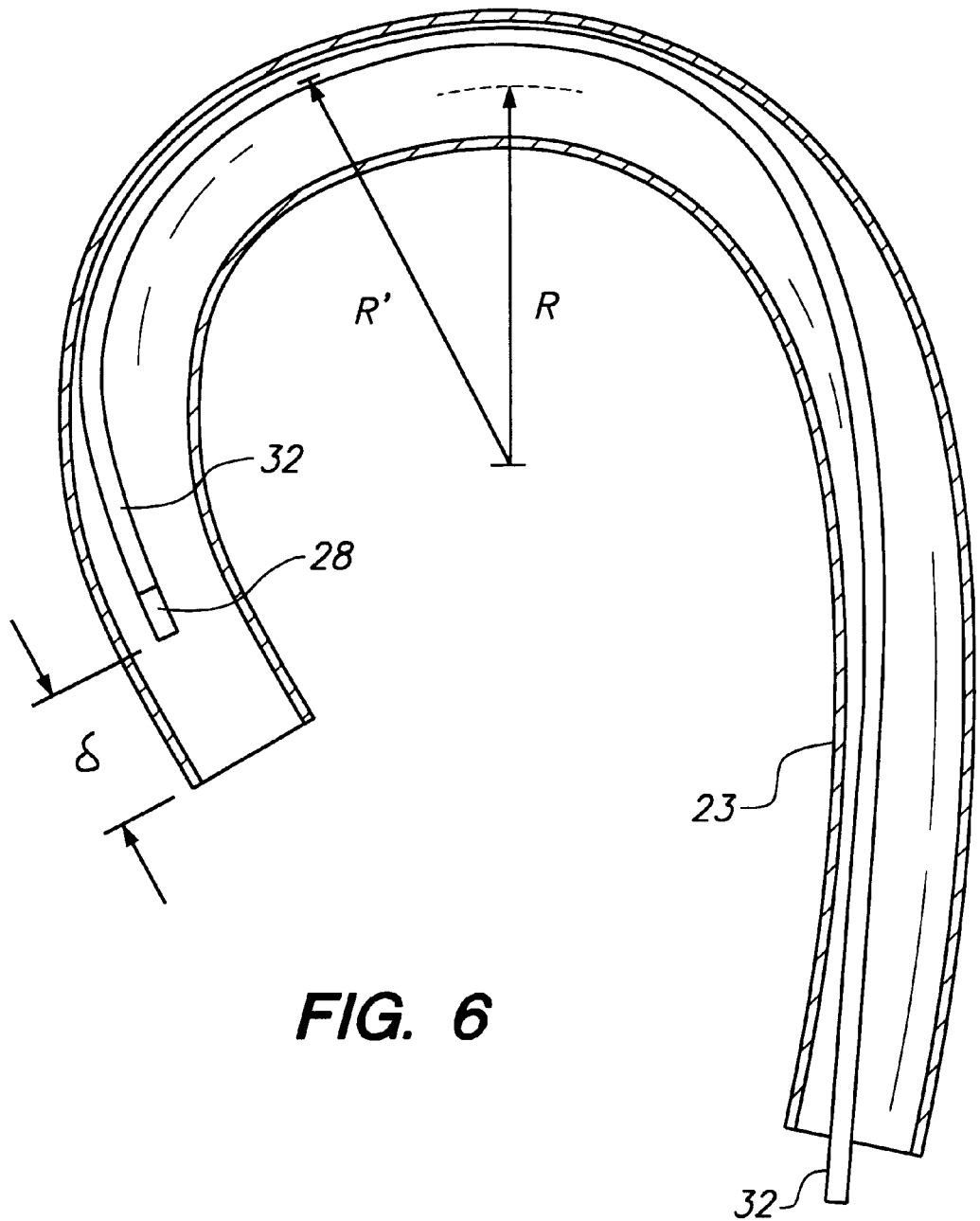
FIG. 6 illustrates how percutaneous insertion of the apparatus of FIG. 1 along a tortuous path causes a variable displacement between the cutting head and distal end face of the inner catheter.

Referring now to FIG. 6, a distal portion of inner catheter 23 is shown being deflected such as may be expected when the distal end of device 21 is percutaneously inserted along a tortuous path. For example, inner catheter 23 is shown as it may be deflected when inserted transluminally via a femoral artery and advanced in a retrograde manner through the aortic arch into the left ventricle. Drive tube 32 and cutting head 28 are shown disposed within inner catheter 23. For purposes of illustration, the discrepancy between the outer diameter of drive tube 32 and the inner diameter of lumen 31 of inner catheter 23 is exaggerated.

As depicted in FIG. 6, because inner catheter 23 has an average radius of curvature R, while the smaller drive tube has a larger radius of curvature R', the degree of tortuosity imposed on the distal end of device 21 causes the distal end of cutting head 28 to move to a variable distance δ from distal endface 40 of inner catheter 23. Because the linear actuator mechanism is configured to advance the cutting head a predetermined distance, the variable distance δ introduced by the degree of tortuosity changes the extend to which cutting head 28 extends beyond distal endface 40 of the inner catheter. This effect is further heightened where the tip of the catheter is articulated using a pull wire that exerts a compressive force on the catheter.

Thus, applicant has discovered that, depending upon the degree of flex imparted to the distal end of device 21, the depth of the cutting channel formed by the cutting head may be undesirably changed an unknown amount. Applicant has therefore determined that if channels are to be formed to a uniform and predetermined depth in the myocardium, a mechanism must be provided to limit and control the maximum extension of the cutting head.

Figure 7A:
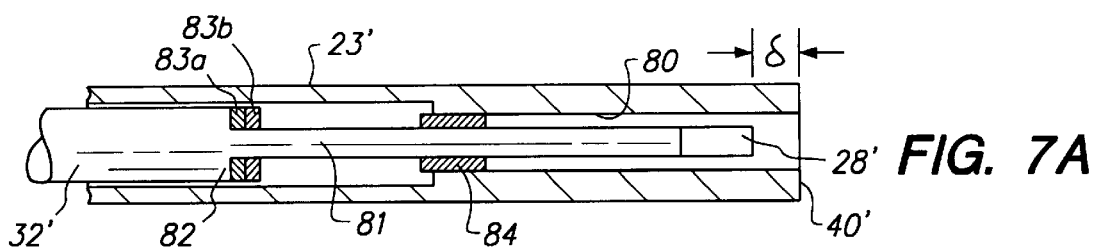
FIGS. 7A and 7B are, respectively, sectional views showing an illustrative mechanism for limiting the maximum extension of the cutting head of the apparatus of FIG. 1.
Figure 7B:
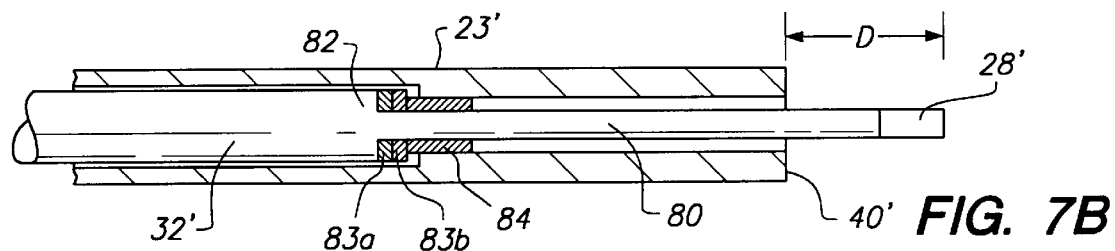

Referring now to FIGS. 7A and 7B, a first embodiment of apparatus and methods for providing a uniform maximum extension of a cutting head are described that overcome the aforementioned problem. In accordance with the principles of the present invention, device 21' having inner catheter 23', drive tube 32' and cutting head 28' is described. Inner catheter 23' is similar to that described hereinabove with respect to FIG. 2 (preformed bend omitted for clarity), except that a distal region of inner catheter 23 has reduced diameter lumen 80. Drive tube 32' includes reduced diameter portion 81 to which cutting head 28' is affixed.

Drive tube 32' forms shoulder 82 where it couples to reduced diameter portion 81. Stainless steel washer 83a is disposed on drive tube 32' between low-friction washer 83b and shoulder 82 of drive tube 32', so that low-friction washer 83b forms a first bearing surface. Rigid tubular member 84, for example, a short section of stainless steel hypotube, is affixed to the interior of lumen 80 of catheter 23' so that its proximal end forms a mating bearing surface to low-friction washer 83b. Washers 83a and 83b and tubular member 84 alternatively may be constructed or coated with a radio-opaque material to aid in visually positioning the drive tube to account for the variable distance created by bending of the catheter.

In accordance with the principles of the present invention, the linear actuator is configured to advance drive wire 63 (see FIG. 4A), and therefore drive tube 32' and cutting head 28' until low-friction washer 83b abuts against the proximal end of rigid tubular member 84. In this manner, drive tube 32' and cutting head 28' are advanced a total distance of δ+D, where δ is the unknown distance caused by differential bending of the drive tube and the inner catheter, and D is the desired maximum extension of cutting head 28' beyond distal endface 40' of inner catheter 23'.

Applicant has determined however, that where forward motion of the drive tube is controlled by a mechanical actuator, some precaution must be made to ensure that forward motion of the linear actuator in controller 25 stops when low-friction washer 83 first contacts rigid member 84. Otherwise, the forward motion of the drive tube might tear the distal end of inner catheter 23' off or cause buckling of drive tube 32'.

Further in accordance with the present invention, monitoring circuitry 75 of controller 25 (see FIG. 5) therefore is adapted to sense a parameter of the motor 74 or linear actuator 73, and to signal linear actuator 73 to cease forward (i.e. distal) motion of the drive tube. This may be accomplished, for example, by monitoring the stall torque of motor 74 e.g., by monitoring the winding current required by that component, or by monitoring the linear displacement or linear force applied by linear actuator 73. Processor 70 may be programmed to then reverse the direction of linear actuator mechanism 73 responsive to the motor parameter of component 73 or 74 exceeding a predetermined threshold. Thus, the cutting head will be retracted as soon as low-friction washer 83b bears against rigid tubular member 84 with sufficient force to cause a disturbance in the monitored parameter for motor 74 or linear actuator 73.

Figure 8:
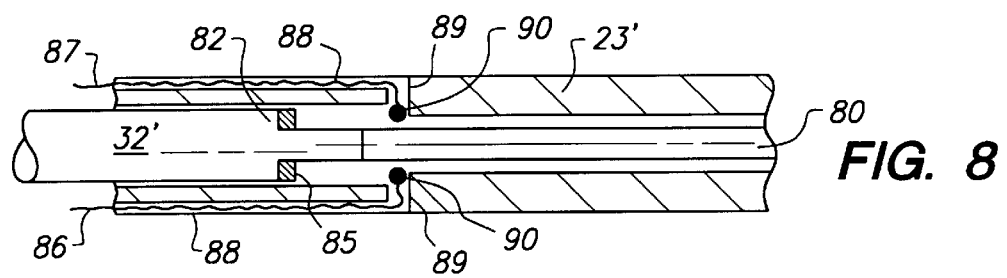
FIG. 8 is a sectional view of an alternative mechanism for limiting the maximum extension of the cutting head of apparatus constructed in accordance with the principles of the present invention.

Referring to FIG. 8, an alternative embodiment for sensing that the maximum cutting depth has been attained is described. Drive tube 32' is coupled to reduced diameter portion 80, and includes electrically conductive washer 85 disposed adjacent to shoulder 82. Electrical lead wires 86 and 87 are disposed in grooves 88 in the outer surface of inner catheter 23'. Lead wires pass through holes 89 and are coupled to electrical contacts 90. When drive tube 32' is advanced in the distal direction, washer 85 bears against contacts 90, thereby completing an electrical circuit that can be sensed by controller 25. When the controller senses that the switch formed by washer 85 and contacts 90 is closed, it signals linear actuator 73 to reverse direction.

Figure 9A:
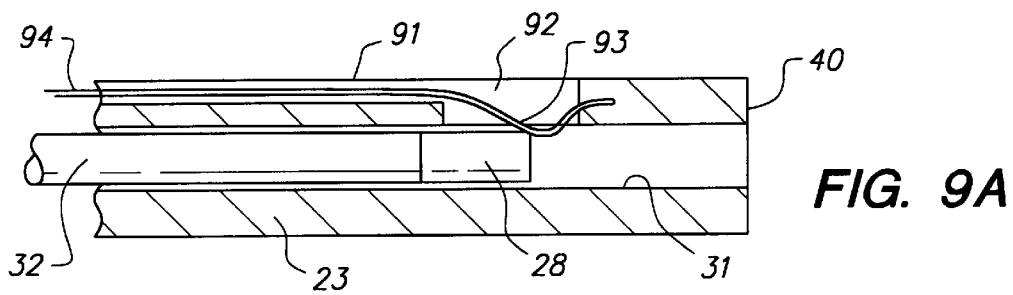
FIGS. 9A and 9B are, respectively, sectional views of other alternative mechanisms for limiting and/or adjusting the maximum extension of the cutting head.

With respect to FIG. 9A, an alternative embodiment is described that permits the variable distance δ imposed by bending of the catheter to be accounted for, and also permits the maximum cutting depth to be adjusted. In this embodiment, which omits a mechanical stop as in the embodiments of FIGS. 7 and 8, inner catheter 23 includes groove 91 with window 92 communicating with lumen 31. Resilient contact element 93 is disposed through window 92 to contact the distal end of cutting head 28. Contact element 93 is configured to deflect upwardly to permit unobstructed distal and proximal movement of cutting head 28 and drive tube 32. Contact element 93 is coupled to one or more electrical wires 94 disposed in groove 91 that couple to controller 25 via handle 24 and cable 26.

In accordance with one aspect of the present invention, contact element 93 provides a signal that is sensed by controller 25 to determine the location of cutting head 28 relative to distal endface 40 of inner catheter 23. Contact element 93 may comprise, for example, a resilient wire element coupled to a strain gauge. Alternatively, contact element 93 may be energized with an electric current to form one part of an electrical switch that is closed when it contacts cutting head 28, also coupled to the electric current by one or more suitable conductors (not shown). Still other mechanisms for detecting the proximity of cutting head 28, such as a Hall effect sensor, may be employed. Accordingly, once the distal end region of inner catheter 23 is disposed within the patient's left ventricle, inner catheter 23 may be adjusted proximally or distally until contact element 93 indicates that the cutting head is located a predetermined distance from distal endface 40.

As a further aspect of the embodiment of FIG. 9A, linear actuator 73 of controller 25 may be programmed to accept a stroke input via input device 36 of controller 25. In this manner, inner catheter 23 may be adjusted to first eliminate the variable distance δ introduced by bending of the inner catheter, e.g., using wheel 44 on handle 24, while the extension of cutting head 28 beyond distal endface 40 of inner catheter 23 may be independently adjusted to a user selected value as a function of the stroke length of linear actuator 73. Alternatively, wheel 44 may be omitted, and linear actuator 73 may be programmed to first "zero out" the variable distance δ using the signal provided from contact element 93, and then accepts a user selectable stroke length that determines the maximum depth of the channel.

Figure 9B:
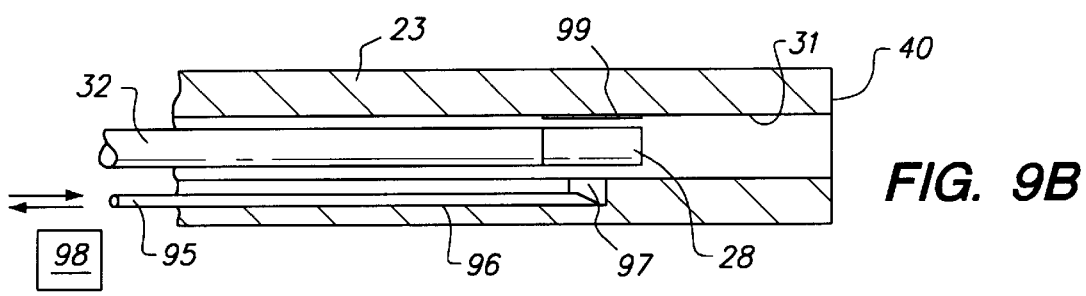

With respect to FIG. 9B, another alternative embodiment for controlling that the maximum cutting depth is described. This embodiment also omits a mechanical stop, and includes inner catheter 23 having fiber optic element 95 disposed in lumen 96. The distal end of fiber optic element 95 is cut at a 45° angle, so that light transmitted along the element is emitted through aperture 97 that opens into lumen 31. Light source 98, e.g., a laser diode, is coupled to the proximal end of fiber optic element 95 by means that are per se known.

Optically absorptive material 99 is disposed on the interior of the opposing wall of the inner catheter, so that light emitted by element 95 is absorbed when the cutting head 28 is fully retracted proximally of aperture 97. When drive tube 32 obscures aperture 97, some of the light emitted by element 95 is reflected back into the distal end of the fiber optic element. This reflected light may be sensed by suitable circuitry in controller 25, and used to signal processor 70 that cutting head 28 is located a predetermined distance from distal endface 40 of inner catheter 23, thereby "zeroing out" the variable distance δ. As for the embodiment of FIG. 9A, linear actuator 73 of controller 25 may be programmed to then provide a maximum cutting depth as a function of the stroke length of the linear actuator, independent of the degree of bending imposed on the inner catheter.

As will of course be understood, still other mechanisms may be used to sense that the location of the cutting head or drive tube relative to the distal endface of inner catheter 23, or some other reference point of distal end region of inner catheter 23. For example, saline or blood introduced into lumen 31 between the cutting head and a pair of electrical leads may be used to sense the location of the cutting head by measuring impedance across the lumen. Still other mechanisms may include, for example, piezoelectric crystals that use ultrasound or measure stress, so long as the mechanisms are sufficiently compact to be disposed near the distal end of the inner catheter without appreciably increasing the overall diameter of the inner catheter.

Figure 10A:
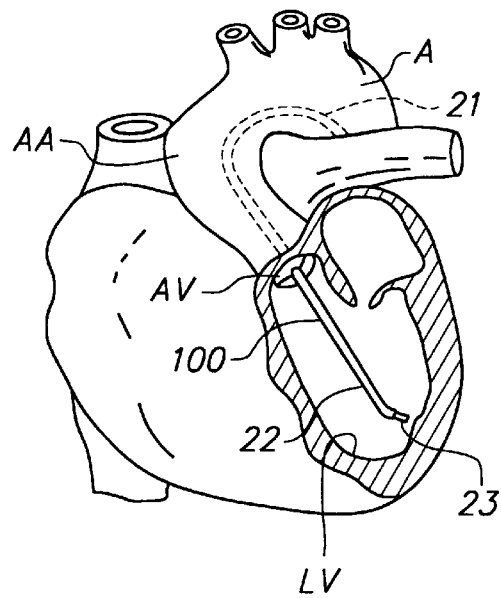
FIGS. 10A–10C are views illustrating deployment and use of the apparatus of FIG. 1 to percutaneously form channels in the myocardium.
Figure 10B:
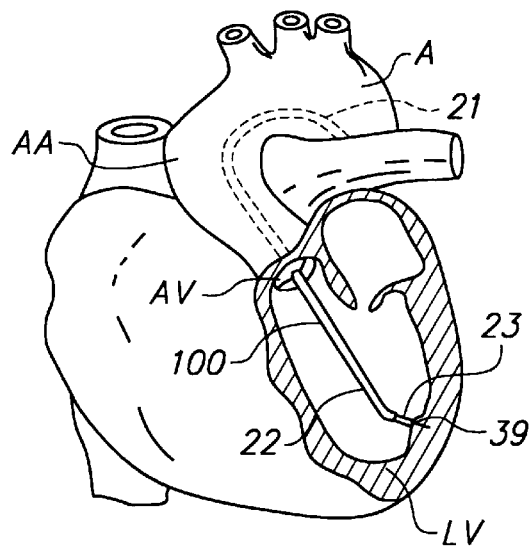
Figure 10C:
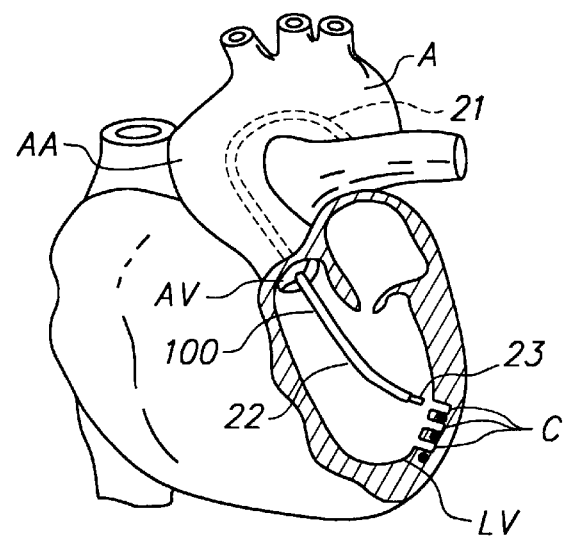

Referring now to FIGS. 10A–10C, a method of using the apparatus of the present invention to percutaneously perform myocardial revascularization is described. In FIG. 10A, distal region 100 of device 21 of FIG. 1 is shown positioned in a patient's left ventricular cavity, using techniques which are per se known. Specifically, distal region 100 of device 21 is inserted via a femoral artery, and is maneuvered under fluoroscopic guidance in a retrograde manner up through the descending aorta, through aortic arch A, and down through ascending aorta AA and aortic valve AV into left ventricle LV. Previously known imaging techniques, such as ultrasound, MRI scan, CT scan, or fluoroscopy, may be used to verify the location of the distal region 100 within the heart.

In FIG. 10B, slider button 41 on handle 24 is advanced to extend needle stabilizer 39 so that it penetrates into the myocardium a predetermined distance, for example, 7 mm. Button 42 on handle 24 then is depressed, causing the drive system of controller 25 to extend cutting head 28 to bore a channel into the myocardium to a predetermined depth. Alternatively, button 42 of handle 24 may be omitted, and controller 25 instead programmed so that linear actuator 73 causes the cutting head to be extended a predetermined interval of time (e.g., 1 second) after slider button 41 is actuated. In this alternative embodiment, slider button 41 will of course have to generate a signal that is communicated to controller 25 via cable 26.

When cutting head 28 engages the endocardium, a reaction force is generated in inner catheter 21 that tends both to push distal region 100 away from the tissue. Needle stabilizer 39 counteracts these reaction forces and reduces transverse movement of the distal end of inner catheter 23, thus retaining the inner catheter in position while the cutting head is extended and retracted. Tissue severed by the cutting head is aspirated to trap 33 of controller 25.

Once cutting head reaches its maximum extension, as determined by any of the means described hereinabove, processor 70 causes forward motion of the cutting head to cease. In the embodiments using linear actuator 73, processor 70 also issues a command to reverse the direction of linear actuator 73. This in turn causes cutting head 28 to be withdrawn from channel C formed in the myocardium to a position just below distal endface 40 of inner catheter 23.

As shown in FIG. 10C, a matrix of spaced-apart channels C may be formed in the wall of left ventricular wall LV by rotating outer guide catheter 22 and inner catheter 23 relative to one another (see FIG. 3). Needle stabilizer 39 and cutting head 28 are then advanced at each position to form further channels C in the tissue. The foregoing methods therefore enable a matrix of channels to be formed in the left ventricular wall. It is believed that such channels may be drilled anywhere on the walls of the heart chamber, including the septum, apex and left ventricular wall, and the above-described apparatus provides this capability.

Figure 11:
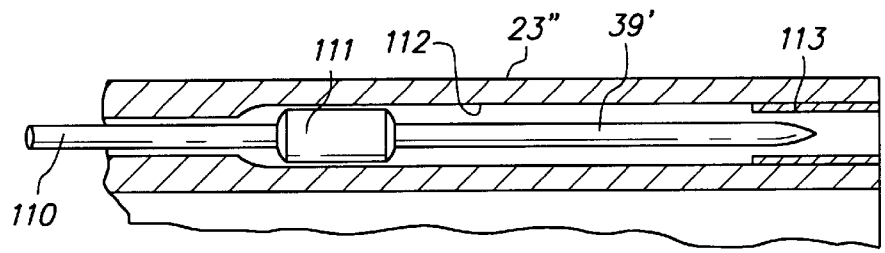
FIG. 11 is a detailed sectional view of a needle stabilizer constructed in accordance with one aspect of the present invention.

Referring to FIG. 11, a preferred embodiment of a needle stabilizer of the present invention is described. Because the needle stabilizer is subject to the same type of flex-induced displacement as the drive tube (as discussed with respect to FIG. 6), it would be desirable to ensure that the needle stabilizer is extended to a predetermined depth, independent of the degree of bending imposed on inner catheter 23.

Needle stabilizer 39' therefore includes push wire 110, such as a Teflon-coated stainless steel wire, having tubular member 111, for example, a short length of stainless steel hypotube, welded to it. Tubular member 110 is disposed in bore 112 of catheter 23", and is captured in bore 112 by member 113. Member 113 is affixed to inner catheter 23", and stops the forward motion of tubular member 111 when slider button 41 is pushed in the distal direction.

Advantageously, tubular member 111 may comprise a radioopaque material, thus ensuring that the location of needle stabilizer 39' is visible under a fluoroscope.

Figure 12A:
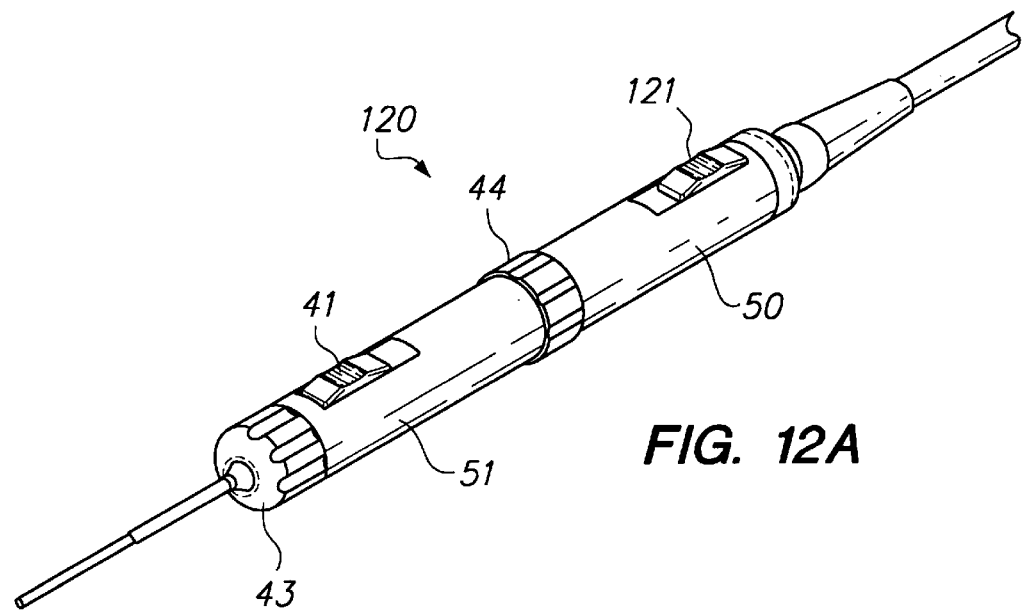
FIGS. 12A and 12B are, respectively, a perspective view and sectional view of a handle of an alternative embodiment of the apparatus of the present invention.
Figure 12B:
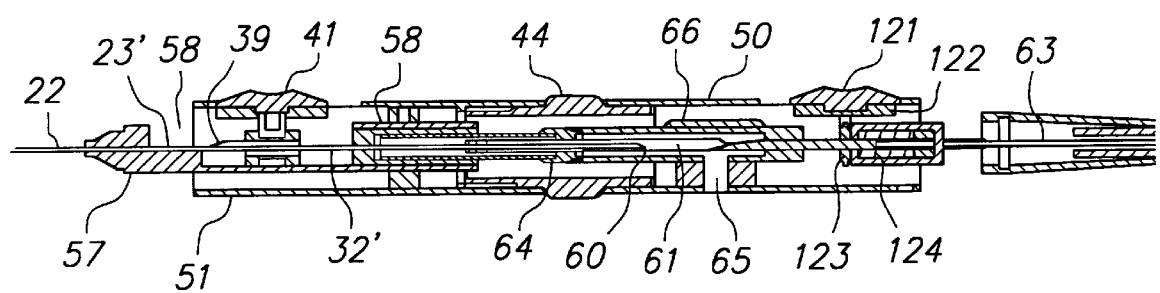

Referring now to FIGS. 12A and 12B, handle 120 of an alternative embodiment of the present invention is described. In this embodiment, linear actuator 73 of controller 25 is omitted, and drive tube 32 and cutting head 28 are instead advanced by slider button 121 of handle 120. Like components of handle 120 with the components of handle 24 of FIGS. 4A and 4B are indicated by like numbers.

Handle 120 differs that instead of having button 42 signal processor 70 to activate linear actuator mechanism, slider button 121 instead includes yoke 122 that is engaged with disk 123 affixed to an extension of drive wire 63. Disk 123 is biased in a proximal position by spring 124. In this embodiment, the drive tube and inner catheter preferably include a mechanical stop, such as shown in FIGS. 7A and 7B. Thus, the clinician can sense when drive tube 32' has abutted against tubular member 84, and may release forward pressure on slider button 121, thereby allowing spring 124 to return the cutting head to its retracted position.

Figure 13A:
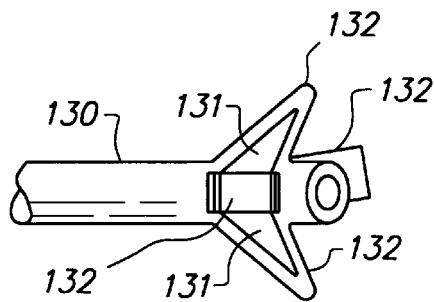
FIGS. 13A–13G are views of distal regions of the inner catheters of alternative embodiments of the present invention.

With respect to FIGS. 13A–13F, alternative embodiments of stabilizer elements suitable for use with device 21 of the present invention are described. In FIG. 13A, the distal end of inner catheter 130 includes a plurality of longitudinal slits 131 that allow the catheter to fold back on itself to form a plurality of stabilizing members 132 when urged against an endocardial surface. Stabilizer members 132 preferably are angled in a distal direction to engage and stabilize the distal end of the inner catheter against the endocardial surface during activation of the cutting head.

Figure 13B:
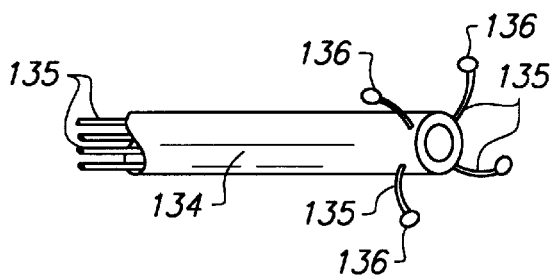

In FIG. 13B, inner catheter 134 includes a plurality of lumens through which preformed wires 135, comprising, for example, a nickel-titanium alloy, are advanced. Each of the preformed wires 135 includes a ball or foot 136 for engaging an endocardial surface to stabilize the inner catheter in contact therewith. Wires 135 may be advanced or retracted singly or as a group.

Figure 13C:
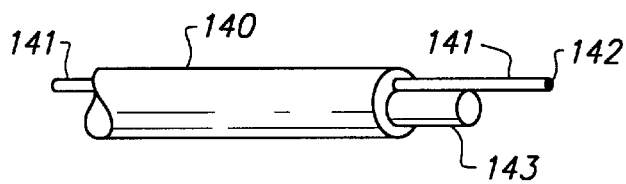

In FIG. 13C, inner catheter 140 includes and alternative embodiment of needle stabilizer 39 of FIG. 2. In this embodiment, needle stabilizer 141 includes lumen 142 that may be coupled, for example, to a syringe containing a therapeutic agent such as a drug, angiogenic factors, gene vectors, plasmids, etc. Needle stabilizer 142 therefore not only serves to stabilize the distal end of inner catheter 140 in contact with the endocardium during activation of the cutting head, but also enables a therapeutic agent to be injected into the tissue prior to, during, or after the channel is formed in the myocardium.

Alternatively, several such needle stabilizers may be arranged around the cutting head to provide enhanced stabilization or multiple injection sites for therapeutic agents, as described hereinafter with respect to FIGS. 15 and 16. As a further alternative, needle stabilizer 141 may be disposed directly adjacent to cutting head 143 (illustrated partly extended) so that the channel formed in the myocardial tissue by cutting head 143 communicates with the needle track formed by needle stabilizer 141. Thus, when cutting head 143 is retracted, lumen 142 of needle stabilizer 141 may be used to inject a therapeutic agent into the channel formed by cutting head 143.

Advantageously, lumen 142 of the embodiment of FIG. 13C permits a therapeutic agent to be injected at locations adjacent to, or directly into, the channel formed by cutting head 143. By comparison, use of a separate needle catheter to inject a therapeutic agent into the myocardium after the channel forming process is completed would result in the therapeutic agent being injected at random locations relative to the previously formed channels.

Figure 13D:
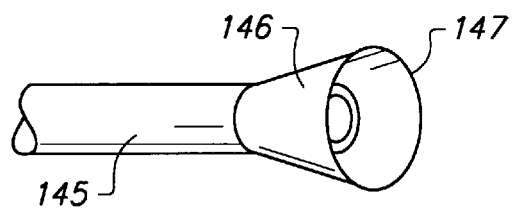

In FIG. 13D, inner catheter 145 includes conical element 146 formed of a resilient material. Conical member 146 may be urged against an endocardial surface so that base 147 provides a larger surface area for stabilizing the inner catheter in contact with the endocardium. In conjunction with suction drawn through the cutting head, conical member 146 may serve as a suction cup for retaining the inner catheter in contact with the endocardial surface.

Figure 13E:
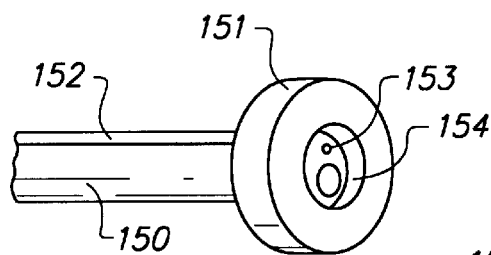

In FIG. 13E, inner catheter 150 includes inflatable member 151 disposed on its distal end for contacting an endocardial surface. Inflatable member 151 is inflated by a suitable inflation medium, such as saline, injected through inflation tube 152. As with the embodiment of FIG. 13D, inflatable member 151 increases the surface area against which the distal end of the inner catheter is stabilized. Moreover, suction may be drawn through lumen 153 so that the inflatable member serves as a suction cup, as in the embodiment of FIG. 13E. Alternatively, lumen 153 may be used to inject a therapeutic agent into cavity 154 formed by inflatable member, and thus serve as a "dam" to direct the therapeutic agent into the channel formed in the myocardium by the cutting head.

Figure 13G:
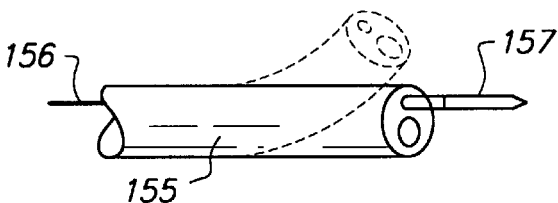
Figure 13F:
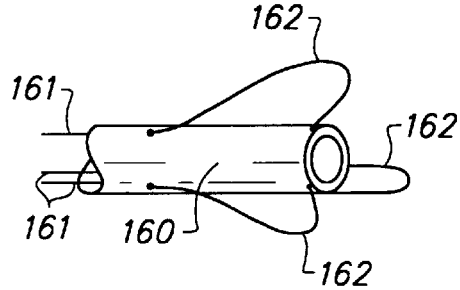

In FIG. 13F, inner catheter 160 includes a plurality of wires 161 that are extended through lumens (not shown) in inner catheter 160 and to form stabilizer legs 162 that stabilize the distal end of the inner catheter against the endocardial surface. Wires 161 may be deployed and retracted individually or in unison. Additional forms of stabilizers comprising extendable wires are describe in the above-incorporated, commonly assigned U.S. Patent.

In FIG. 13G, inner catheter 155 includes pull wire 156 slidingly embedded disposed in a lumen (not shown) and affixed to the distal end of the inner catheter. In this embodiment, instead of inner catheter having a preformed bend, pull wire 156 is instead pulled in a proximal direction to direct the distal end of inner catheter 155 to a desired location on the endocardial surface. Inner catheter 155 may in addition include needle stabilizer 157 such as described hereinabove with respect to FIG. 2.

Figure 14A:
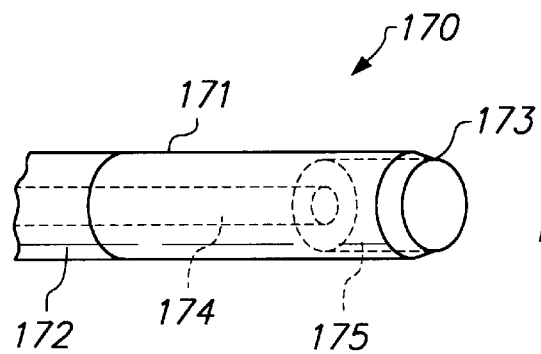
FIGS. 14A–14E are partial perspective views of alternative embodiments of cutting heads of the present invention.

Referring now to FIGS. 14A–14E, alternative embodiments of cutting heads constructed in accordance with the present invention are described. In FIG. 14A, cutting head 170 comprises tubular member 171 affixed to drive tube 172 having sharpened beveled edge 173 and lumen 174. Cutting head 170 includes enlarged diameter region 175 that communicates with lumen 174. It is believed that the presence of the step between enlarged diameter region 175 and lumen 174 will enhance morcellation and aspiration of tissue severed by cutting head 170. In particular, when the core of tissue in enlarged diameter region 175 contacts the smaller diameter of lumen 174, the tissue core is twisted off at its base.

Figure 14B:
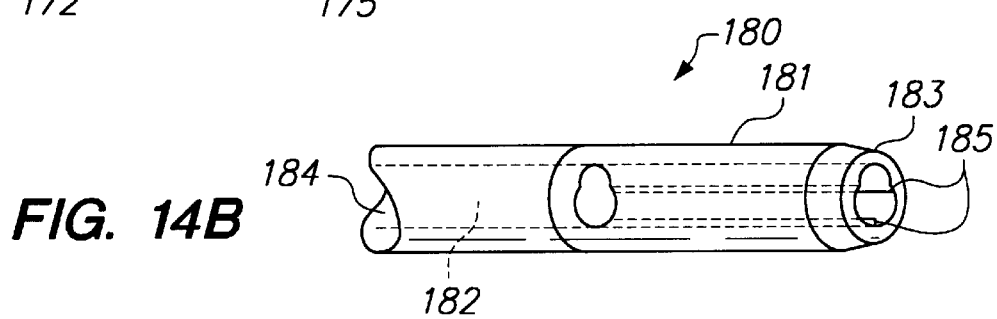

In FIG. 14B, cutting head 180 comprises tubular member 181 affixed to drive tube 182 and having sharpened edge 183 and lumen 184. Cutting head 180 includes a plurality of flutes or grooves 185 extending along lumen 184 that are expected to enhance friction between the cutting head and the severed tissue, thereby enhancing morcellation and aspiration of tissue severed by cutting head 180.

Figure 14C:
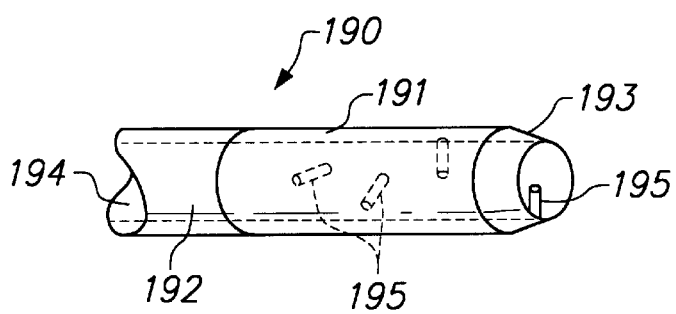

In FIG. 14C, cutting head 190 comprises tubular member 191 affixed to drive tube 192 and having sharpened edge 193 and lumen 194. Cutting head 190 includes a plurality of pins 195 that extend into lumen 194. It is expected that pins 195 will shred the severed tissue core as the cutting head rotates, thereby enhancing aspiration of tissue severed by cutting head 190.

Figure 14D:
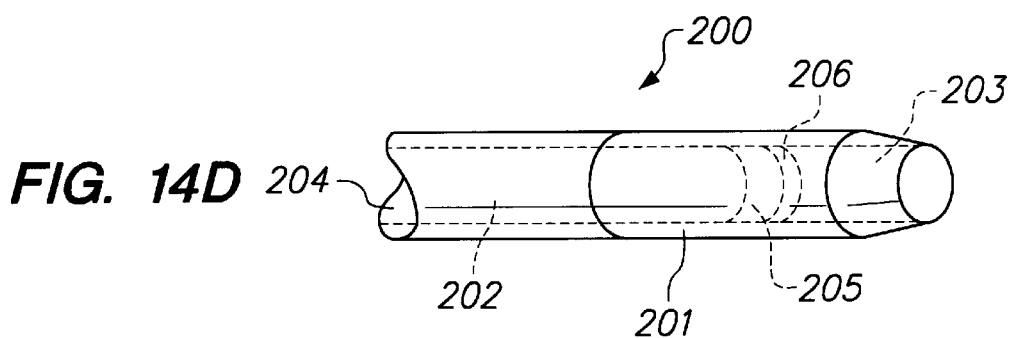

In FIG. 14D cutting head 200 comprises tubular member 201 affixed to drive tube 202 and having sharpened edge 203 and lumen 204. Cutting head 200 includes band 205 having sharpened edge 206 that spans the interior into lumen 204, and which is expected to shred the severed tissue core as the cutting head rotates, thereby enhancing aspiration of tissue severed by cutting head 200.

Figure 14E:
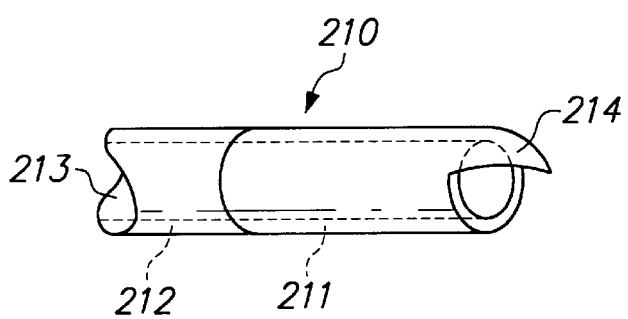

With respect to FIG. 14E, cutting head 210 comprises tubular member 211 affixed to drive tube 212 and having lumen 213. Cutting head 210 includes sharpened element 214 that extends from distal endface 215 of the cutting head. Sharpened element 214 is expected to shred the myocardial tissue as the cutting head is rotated and extended, thus improving aspiration of tissue severed by the cutting head.

Referring to FIGS. 15A–15B and 16A–16B, further alternative embodiments of the device of FIG. 13C are described. In FIGS. 15A and 15B, inner catheter 220 includes multiple needle stabilizers 221 that may be retractable extended from distal endface 222. Each of needle stabilizers 222 includes lumen 223 that may be coupled to a source of therapeutic agent to inject such material into the myocardium at locations adjacent to the channel cut by a cutting head (not shown) extended from lumen 224 of inner catheter 220. In the embodiment of FIGS. 15A and 15B, needle stabilizers 221 diverge from axis 225 of the cutting head.

In FIGS. 16A and 16B, a further alternative of the embodiment of FIGS. 15 is depicted. Inner catheter 230 comprises central lumen 231 having extendable cutting head 232 (shown in the extended position) and converging reciprocable needle stabilizers 233. Each of needle stabilizers 233 preferably includes lumen 234 for injecting a therapeutic agent into the myocardial tissue distal to the maximum depth achieved by cutting head 232. Needle stabilizers optionally also may include side ports 234a. Alternatively, needle stabilizers 233 may be configured to converge just at the distal end of the channel formed by cutting head 232, so that material injected through lumens 234 enters the channel formed by the cutting head. As a yet further alternative, needle stabilizers 233 may be used to inject a bolus of fluid, such as saline, prior to or during the channel forming process to facilitate aspiration of the myocardium severed by cutting head 232.

Referring now to FIGS. 17 and 18, apparatus constructed in accordance with a further feature of the present invention are described. With respect to FIG. 17, apparatus similar to that of FIG. 1 includes inner catheter 240 having reciprocable needle stabilizers 241 disposed on either side of lumen 242 that houses the cutting head. Each of needle stabilizers 241 includes lumen 243 and comprises an electrically conductive material, e.g., stainless steel, and is coupled via conductors 244 to monitoring circuit 245. Sensing circuit 245, which preferably measures a physiologic parameter of the myocardium, is in turn coupled to processor 70 of controller 25.

In one embodiment, sensing circuit 245 may sense electrical activity (e.g., EKG or impedance) in the myocardium between needle stabilizers 241 and generate a signal that is displayed to the clinician operating the instrument. Thus, in accordance with one aspect of the methods of the present invention, the clinician may dispose inner catheter against a region of tissue, deploy needle stabilizers 241, and obtain a reading of the degree of electrical activity in that region of the myocardium.

If the sensed electrical activity is low, indicating that the tissue region is heavily infarcted, the clinician may forego boring a channel. Instead, the clinician may instead simply re-position the distal end of the catheter in contact with another region of tissue more likely to experience a beneficial effect from myocardial revascularization. Likewise, the clinician also may use the sensed physiological parameter as an aid in determining whether to inject therapeutic agents via lumens 243.

Referring to FIG. 18, an alternative embodiment of the device of FIG. 17 is described. In this embodiment the apparatus includes inner catheter 250 having electrically conductive end cap 251. Cutting head 252 (shown in the extended position) is disposed for reciprocation in lumen 253 of inner catheter 250. Needle stabilizer 254 includes injection lumen 255 and dielectric coating 256 over its proximal length. End cap 251 and uninsulated distal region 257 of needle stabilizer are coupled via electrical conductors 258 to sensing circuit 259. A reference electrode (not shown), e.g., a grounding pad, may be coupled to the patient at a remote location. As for the embodiment of FIG. 17, sensing circuit 259 is coupled to processor 70 of controller 25 and is configured to sense or measure a physiologic property of the tissue.

In the embodiment of FIG. 18, sensing circuit 259 preferably measures and displays a signal corresponding to the electrical impedance of the material sensed between the endcap and reference electrode. Thus, for example, a signal generated by sensing circuit 259 may be used by the clinician to determine when the distal end of the inner catheter is in contact with tissue. In addition, by deploying needle stabilizer 254 and measuring and displaying a metric corresponding to the impedance between end cap 251 and uninsulated region 257 of needle stabilizer 255, the clinician may be able to assess the viability of the tissue.

Further in accordance with the methods of the present invention, if the sensed electrical impedance indicates that the tissue region is heavily infarcted, the clinician may forego boring a channel at that location. Instead, the clinician may instead reposition the distal end of the catheter in contact with another region of tissue more likely to experience a beneficial effect from myocardial revascularization. Also, the clinician may use the sensed impedance level (or other physiologic parameter) as an aid in determining whether to inject therapeutic agents via lumens 255.

While preferred illustrative embodiments of the invention are described, it will be apparent that various changes and modifications may be made therein without departing from the invention, and the appended claims are intended to cover all such changes and modifications that fall within the true spirit and scope of the invention.

What is claimed is:

1. Apparatus for percutaneously performing myocardial revascularization comprising:
    a first catheter adapted for insertion into the left ventricle, the first catheter having a lumen and a distal endface movable to a plurality of sites on an endocardial surface;
    a stabilizer element disposed on the first catheter, the stabilizer element contacting the endocardial surface to stabilize the first catheter against the endocardial surface;
    a cutting head disposed movable from a retracted position within the lumen of the first catheter to an extended position wherein the cutting head extends beyond the distal endface of the first catheter to form a channel in cardiac tissue; and
    means for sensing a physiologic state of cardiac tissue in a region adjacent to the distal endface of the first catheter.

2. The apparatus of claim 1 wherein a distal region of the first catheter further comprises a preformed bend.

3. The apparatus of claim 1 wherein the first catheter further comprises a pull wire for directing the distal endface of the first catheter.

4. The apparatus of claim 1 further comprising a second catheter adapted for insertion into the left ventricle, the second catheter having a preformed bend and a lumen for accepting the first catheter therethrough.

5. The apparatus of claim 1 further comprising means for adjusting a maximum cutting depth of the cutting head.

6. The apparatus of claim 1 wherein the stabilizer element comprises a first retractable needle.

7. The apparatus of claim 6 wherein the distal end of the first catheter comprises an electrically conductive end cap, the means for sensing comprising circuitry for measuring an electrical impedance of cardiac tissue between the end cap and a reference electrode located at a remote position.

8. The apparatus of claim 6 wherein the distal end of the first catheter comprises an electrically conductive end cap, and the means for sensing comprises circuitry for measuring an electrical impedance of cardiac tissue disposed between the end cap and the first retractable needle.

9. The apparatus of claim 6 wherein the stabilizer element further comprises a second retractable needle, the means for sensing comprising circuitry for measuring a physiologic state of cardiac tissue disposed between the first and second retractable needles.

10. The apparatus of claim 9 wherein the physiologic state comprises one of: a degree of electrical activity within the cardiac tissue or an electrical impedance of the cardiac tissue.

11. The apparatus of claim 6 wherein the first retractable needle is curved towards or away from a longitudinal axis of the cutting head.

12. The apparatus of claim 6 wherein the first retractable needle includes a lumen having one or more ports adapted for injecting a therapeutic agent into the cardiac tissue.

13. The apparatus of claim 1 further comprising means for limiting extension of the cutting head in the extended position.

14. The apparatus of claim 13 wherein the means for limiting extension comprises an electrical circuit that senses when the cutting head is disposed a predetermined distance from the distal endface of the first catheter.

15. The apparatus of claim 14 wherein the electrical circuit further comprises one of: a fiber optic element, a resilient contact member, a strain gauge, a Hall effect sensor or an electrically conductive fluid.

16. The apparatus of claim 13 wherein the means for limiting extension further comprises monitoring circuitry for monitoring a motor parameter and generating a signal that causes movement of the cutting head towards the extended position to cease when the motor parameter exceeds a predetermined threshold.

17. The apparatus of claim 1 wherein the stabilizer element comprises one of: a plurality of stabilizing members adapted to be adjusted between a contracted state and an expanded state, an inflatable member, and a plurality of sections of the first catheter that fold back on themselves when the distal endface is urged against an endocardial surface.

18. The apparatus of claim 1 further comprising drive means for rotating the cutting head and a linear actuator that translates the cutting head from the retracted position to the extended position.

19. The apparatus of claim 1 wherein the cutting head comprises a tubular member having a lumen through which cardiac tissue severed by the cutting head is aspirated, the cutting head further comprising one of: a stepped portion disposed between the lumen and a distal endface of the cutting head, a plurality of flutes or grooves disposed along an interior surface of the lumen, a member that projects within the lumen, and a sharpened element extending from a distal endface of the cutting element.

20. Apparatus for percutaneously performing myocardial revascularization comprising:
    a first catheter adapted for insertion into the left ventricle, the first catheter having a cutting head lumen, a needle lumen, and a distal endface movable to a plurality of sites on an endocardial surface;
    a first needle disposed on the first catheter movable from a retracted position within the needle lumen to an extended position extending beyond a distal endface of the first catheter, the first needle contacting and penetrating the endocardial surface to stabilize the first catheter against the endocardial surface; and
    a cutting head disposed movable from a retracted position within the lumen of the first catheter to an extended position wherein the cutting head extends beyond the distal endface of the first catheter to form a channel in cardiac tissue.

21. The apparatus of claim 20 wherein the first needle includes a lumen having one or more ports adapted for injecting a therapeutic agent into the cardiac tissue.

22. The apparatus of claim 20 wherein the distal end of the first catheter comprises an electrically conductive end cap, the apparatus further comprising sensing circuitry for measuring an electrical impedance of cardiac tissue between the end cap and a reference electrode at a remote location.

23. The apparatus of claim 20 wherein the distal end of the first catheter comprises an electrically conductive end cap, the apparatus further comprising sensing circuitry for measuring an electrical impedance of cardiac tissue disposed between the end cap and the first needle.

24. The apparatus of claim 20 wherein further comprising a second needle mounted for extension and retraction from the distal endface of the first catheter, the apparatus further comprising sensing circuitry for measuring a physiologic state of cardiac tissue disposed between the first and second needles.

25. The apparatus of claim 24 wherein the physiologic state comprises one of: a degree of electrical activity within the cardiac tissue or an electrical impedance of the cardiac tissue.

26. The apparatus of claim 20 wherein a distal region of the first catheter further comprises a preformed bend, the apparatus of further comprising a second catheter adapted for insertion into the left ventricle, the second catheter having a preformed bend and a lumen for accepting the first catheter therethrough.

27. The apparatus of claim 20 further comprising means for adjusting a maximum cutting depth of the cutting head.

28. The apparatus of claim 20 further comprising means for limiting extension of the cutting head in the extended position.

29. The apparatus of claim 20 wherein the cutting head comprises a tubular member having a lumen through which cardiac tissue severed by the cutting head is aspirated, the cutting head further comprising one of: a stepped portion disposed between the lumen and a distal endface of the cutting head, a plurality of flutes or grooves disposed along an interior surface of the lumen, a plurality of pins projecting within the lumen, a sharpened band disposed within and spanning the lumen, and a sharpened element extending from a distal endface of the cutting element.

30. A method of percutaneously performing revascularization of a patient's cardiac tissue, the method comprising:
    providing a first catheter adapted for insertion into the left ventricle comprising a stabilizer element and a cutting head movable from a retracted position to an extended position;
    advancing a distal region of the first catheter transluminally to a position within a patient's left ventricle;
    deploying the stabilizer element to stabilize the distal region of the first catheter in contact with an endocardial surface;
    sensing a physiologic state of cardiac tissue in a portion of the cardiac tissue adjacent to the distal endface of the first catheter; and
    if it is determined that myocardial revascularization in the portion of cardiac tissue adjacent to the distal endface would have a beneficial effect, advancing the cutting head from the retracted to the extended position to bore a channel into the patient's cardiac tissue.

31. The method of claim 30 wherein the stabilizer element comprises a first retractable needle and deploying the stabilizer element comprises advancing the first retractable needle to penetrate into the patient's cardiac tissue.

32. The method of claim 31 wherein the distal end of the first catheter comprises an electrically conductive end cap, and sensing a physiologic state further comprises measuring an electrical impedance of cardiac tissue between the end cap and a reference electrode located at a remote location.

33. The method of claim 32 wherein the distal end of the first catheter comprises an electrically conductive end cap, and sensing a physiologic state further comprises measuring an electrical impedance of cardiac tissue disposed between the end cap and the first retractable needle.

34. The method of claim 33 further comprising comparing a measured value of electrical impedance of the cardiac tissue to a predetermined threshold to decide whether to advance the cutting head or re-position the first catheter.

35. The method of claim 31 wherein the stabilizer element further comprises a second retractable needle, and sensing a physiologic state further comprises measuring a physiologic state of cardiac tissue disposed between the first and second retractable needles.

36. The method of claim 35 wherein measuring a physiologic state comprises measuring one of: a degree of electrical activity within the cardiac tissue or an electrical impedance of the cardiac tissue.

37. The method of claim 36 further comprising determining a degree of infarction based on the measured value of the physiologic state of the cardiac tissue.

38. The method of claim 31 wherein the first retractable needle includes a lumen having one or more ports, the method further comprising injecting a therapeutic agent into the cardiac tissue through the lumen via the one or more ports.

39. The method of claim 31 further comprising aspirating cardiac tissue severed by the cutting head.

40. A method of percutaneously performing revascularization of a patient's cardiac tissue, the method comprising:
    providing a first catheter adapted for insertion into the left ventricle comprising a first needle movable from a retracted position to an extended position and a cutting head movable from a retracted position to an extended position;

advancing a distal region of the first catheter transluminally to a position within a patient's left ventricle;

advancing the first needle to the extended position to penetrate and stabilize the distal region of the first catheter in contact with an endocardial surface;

rotating the cutting head; and advancing the cutting head from the retracted to the extended position to bore a channel into the patient's cardiac tissue.

41. The method of claim 40 wherein the first needle includes a lumen having one or more ports, the method further comprising injecting a therapeutic agent into the cardiac tissue through the lumen via the one or more ports.

42. The method of claim 40 wherein the first catheter further comprises a second needle movable from a retracted position to an extended position, the method further comprising measuring a physiologic state of cardiac tissue disposed between the first and second needles.

43. The method of claim 42 wherein measuring a physiologic state comprises measuring one of: a degree of electrical activity within the cardiac tissue or an electrical impedance of the cardiac tissue.

44. The method of claim 42 further comprising determining a degree of infarction based on the measured value of the physiologic state of the cardiac tissue.

45. The method of claim 40 further comprising aspirating cardiac tissue severed by the cutting head.

* * * * *

UNITED STATES PATENT AND TRADEMARK OFFICE
CERTIFICATE OF CORRECTION

PATENT NO. : 6,102,926
DATED : August 15, 2000
INVENTOR(S) : Tartaglia et al.

It is certified that error appears in the above-identified patent and that said Letters Patent is hereby corrected as shown below:

<u>Title page,</u>
Item [56], References Cited, OTHER PUBLICATIONS, in citations from "*www.cardiogenesis.com*", please delete all three appearances of "198" and insert -- TM --.
"Kohmoto, Takushi, M.D.," reference, please delete "Transmyocardial Lase Channels" and insert -- Transmyocardial Laser Channels --.
"Sen, P.K. et al.," reference, please delete "vol. 62" and insert -- vol. 64 --.
"Thaning, Otto," reference, please delete "No. 9" and insert -- No. 8 --.

Signed and Sealed this

Twentieth Day of January, 2004

JON W. DUDAS
*Acting Director of the United States Patent and Trademark Office*